United States Patent [19]
Cohen et al.

[11] Patent Number: 5,397,360
[45] Date of Patent: Mar. 14, 1995

[54] MODULAR COMPONENTS FOR PROSTHETIC IMPLANTS

[75] Inventors: Robert C. Cohen, Rockaway; Scott V. Cron, Bloomfield, both of N.J.

[73] Assignee: Osteonics Corp., Allendale, N.J.

[21] Appl. No.: 16,868

[22] Filed: Feb. 11, 1993

[51] Int. Cl.6 .................... A61F 2/28; A61F 2/38
[52] U.S. Cl. ...................... 623/16; 623/18; 623/20; 623/23
[58] Field of Search ........ 623/16, 18, 20, 22, 623/11, 66

[56] References Cited

U.S. PATENT DOCUMENTS

| | | |
|---|---|---|
| 521,861 | 6/1894 | Zeiser et al. |
| 3,953,143 | 4/1976 | Friedline et al. |
| 4,187,559 | 2/1980 | Grell et al. |
| 4,257,129 | 3/1981 | Volz |
| 4,318,190 | 3/1982 | Cortesi |
| 4,662,889 | 5/1987 | Zichner et al. |
| 4,822,366 | 4/1989 | Bolesky ............... 623/20 |
| 4,834,081 | 5/1989 | Van Zile ............. 623/20 X |
| 4,892,547 | 1/1990 | Brown |
| 4,936,853 | 6/1990 | Fabian et al. |
| 4,938,769 | 7/1990 | Shaw |
| 4,944,757 | 7/1990 | Martinez et al. |
| 4,959,071 | 9/1990 | Brown et al. |
| 5,019,103 | 5/1991 | Van Zile et al. |
| 5,053,036 | 10/1991 | Perren et al. ............ 606/71 X |
| 5,061,271 | 10/1991 | Van Zile |
| 5,064,437 | 11/1991 | Stock et al. |
| 5,080,674 | 1/1992 | Jacobs et al. |
| 5,080,676 | 1/1992 | May |

FOREIGN PATENT DOCUMENTS

| | | | |
|---|---|---|---|
| 0010527 | 4/1980 | European Pat. Off. | |
| 0552950 | 7/1993 | European Pat. Off. | 623/20 |

*Primary Examiner*—David Isabella
*Attorney, Agent, or Firm*—Samuelson & Jacob

[57] ABSTRACT

A modular component for a prosthetic implant includes a first member, in the form of a tibial tray member, and a second member, in the form of a stem member, joined together by the insertion of a tapered post on the stem member into a tapered receptacle in the tibial tray member, the relative tapers and relative dimensions of the post and the receptacle being such that the inner surface of the receptacle is seated against the outer surface of the post at least adjacent one end of the receptacle and the corresponding end of the post, and a stabilizing mechanism urges annular segments of the post, adjacent the other end of the post, toward engagement with the inner surface of the receptacle adjacent the corresponding other end of the receptacle to stabilize the connection between the tibial tray member and the stem member.

20 Claims, 3 Drawing Sheets

MODULAR COMPONENTS FOR PROSTHETIC IMPLANTS

The present invention relates generally to prosthetic implants and pertains, more specifically, to prosthetic implants of the type in which at least one component of the implant is assembled from selected parts to construct a component fitted essentially to the needs of a particular recipient.

More recent developments in the implant of prostheses have shown that it is desirable to have available prosthetic implant components constructed of individual alternate parts so that a surgeon may select certain parts for assembly into a component fitted more closely to the requirements of a particular recipient of the prosthetic implant. Thus, for example, tibial components for prosthetic knee implants have been proposed in which the tibial tray member and the tibial stem member are constructed as separate parts selectively joined together to assemble a complete tibial component. In this manner, one of several alternate tibial tray members may be selected for assembly with one of several alternate stem members to provide an essentially custom fitted tibial component.

Since the performance and effectiveness of a prosthetic implant relies to a considerable extent upon the stability of the components in the implanted prosthesis, it is essential that, once assembled, the parts of each component be joined in an assembly so integrated as to preclude instability among the assembled parts. Thus, it becomes essential that the mechanism which joins together the members of a component, such as the tibial tray member and the stem member of a prosthetic knee implant, does so in a manner which assures the stable integrity of the assembly and maintains that stable integrity throughout the service life of the prosthesis. Further, the joining mechanism must be relatively easy to use, both for assembly at the time of implant and for subsequent disassembly, should it become necessary later to dismantle the component for replacement.

The present invention provides an improvement in a modular component for a prosthetic implant in which the mechanism for joining together the members selected for assembly into an integrated implant component attains improved stability between the assembled members. As such, the present invention attains several objects and advantages, some of which are summarized as follows: Provides improved integrity in the connection between the members selected for assembly into an integrated component of a prosthetic implant so as to provide enhanced stability in the completed assembly; enables ease of assembly for facilitating the joining together of selected parts into an integrated component fitted more closely to the requirements of a particular recipient, without sacrificing the stability provided previously only in unitary, one-piece components; employs a minimum number of individual parts of relatively simple construction for relatively economical manufacture and use; promotes reliability for exemplary performance throughout an extended service life.

The above objects and advantages, as well as further objects and advantages, are attained by the present invention, which may be described briefly as an improvement in a modular component for a prosthetic implant, in which modular component a first member and a second member are joined to establish an integrated implant component, the improvement comprising: a post on one of the members, the post extending longitudinally between a first end and a second end spaced away from the first end in a longitudinal direction, the post including an outer surface having a longitudinally tapered surface portion at least adjacent one of the ends of the post and a further surface portion adjacent the other of the ends of the post; a receptacle in the other one of the members for reception of the post when the members are joined, the receptacle extending between a first end and a second end spaced away from the first end in the longitudinal direction, the receptacle including an inner surface having a first surface portion adjacent one of the ends of the receptacle and generally complementary to the tapered surface portion of the outer surface of the post, and a second surface portion adjacent the other of the ends of the receptacle and for juxtaposition with the further surface portion of the outer surface of the post when the first surface portion of the inner surface of the receptacle is seated against the tapered surface portion of the outer surface of the post; laterally deflectable elements for placement adjacent the further portion of the outer surface of the post and the second surface portion of the inner surface of the receptacle when the first surface portion of the inner surface is seated against the tapered surface portion of the outer surface of the post; and operator means for urging the laterally deflectable elements laterally toward engagement-of the further surface portion of the outer surface of the post with the second surface portion of the inner surface of the receptacle, when the first surface portion of the inner surface is seated against the tapered surface portion of the outer surface, to preclude relative movement between the second surface portion and the further surface portion and thereby stabilize the connection between the first member and the second member in the integrated implant component.

The invention will be understood more fully, while still further objects and advantages will become apparent, in the following detailed description of preferred embodiments of the invention illustrated in the accompanying drawing, in which.

Figure 1:
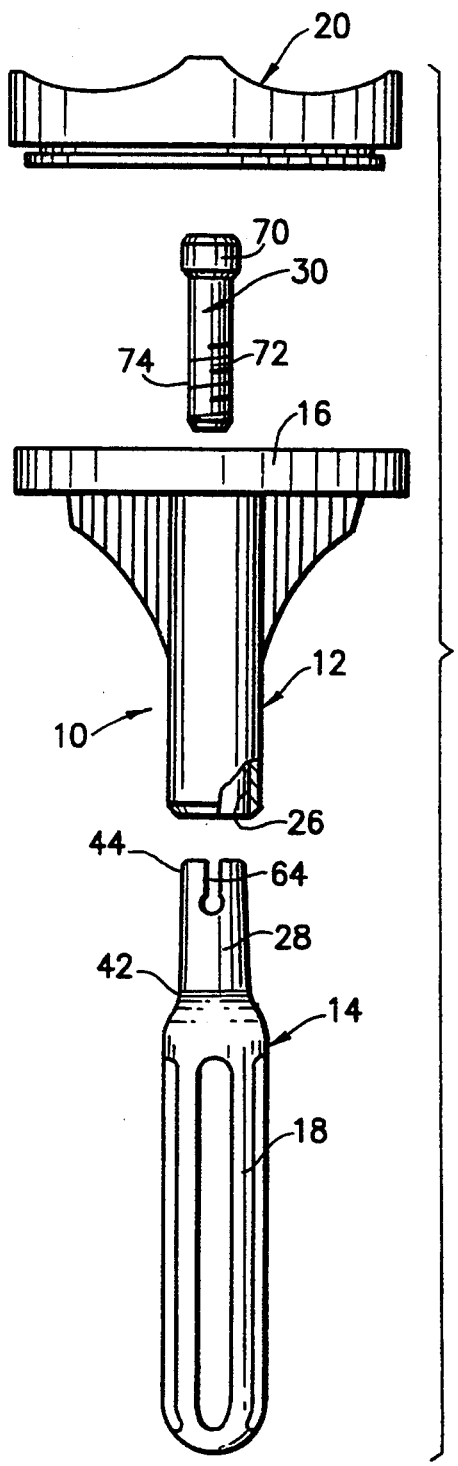
FIG. 1 is an exploded front elevational view of an implant component in the form of a tibial component employing the improvement of the present invention.
Figure 2:
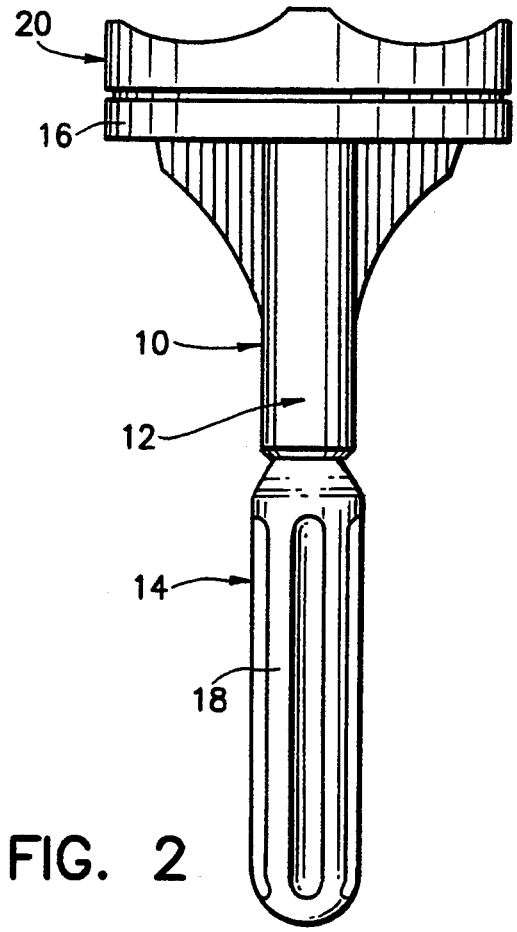
FIG. 2 is a front elevational view of the tibial component assembled.
Figure 3:
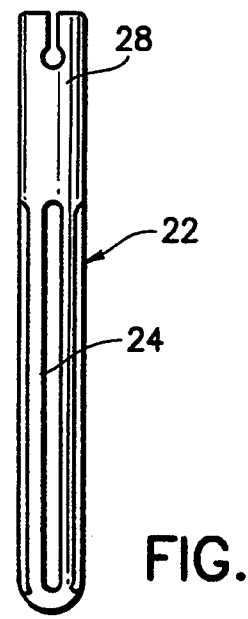
FIG. 3 is a front elevational view of an alternate stem member capable of being selected for assembly as a part of the tibial component.

Referring now to the drawing, and especially to FIGS. 1 and 2 thereof, a modular implant component constructed in accordance with the invention is illustrated in the form of a tibial component 10 for use in a prosthetic knee implant and is seen to include a first member in the form of a tibial tray member 12 and a second member in the form of a stem member 14. The tray member 12 includes a laterally extending tibial tray 16 and the stem member 14 includes a longitudinally extending stem 18. When assembled into an integrated tibial component 10, as seen in FIG. 2, the stem 18 is received within the tibia of a recipient and the tibial tray 16 provides a platform for a tibial bearing member 20, all as is now well known in prosthetic knee implants. Since requirements differ among different recipients, the modular tibial component 10 allows a more accurate fit by enabling the selection of one of several alternate combinations of tibial tray members, stem members and tibial bearing members, as dictated by the requirements of a particular recipient. Thus, for example, the tibial tray member 12 may be assembled with either the stem member 14 or an alternate stem member 22, illustrated in FIG. 3, having a stem 24 of dimensions different from the corresponding dimensions of stem 18. To that end, tibial tray member 12 includes a receptacle 26 and each stem member 14 and 22 includes a post 28 which is received within receptacle 26 for assembly of a selected stem member 14 or 22 with the tibial tray member 12. As seen in FIG. 2, the selected stem member 14 has been assembled with tibial tray member 12 to establish an integrated tibial component 10 for a prosthetic knee implant. The preferred material for the tibial tray member 12 and for the stem member 14 is a biocompatible metal alloy, such as a cobalt-chrome alloy now in common use. The tibial bearing member 20 preferably is constructed of a biocompatible material having appropriate lubricity characteristics, such as a high density polyethylene. An operator member 30 is employed to attain stability in the connection between the tibial tray member 12 and the selected stem member 14, as will be described in detail below.

Figure 4:
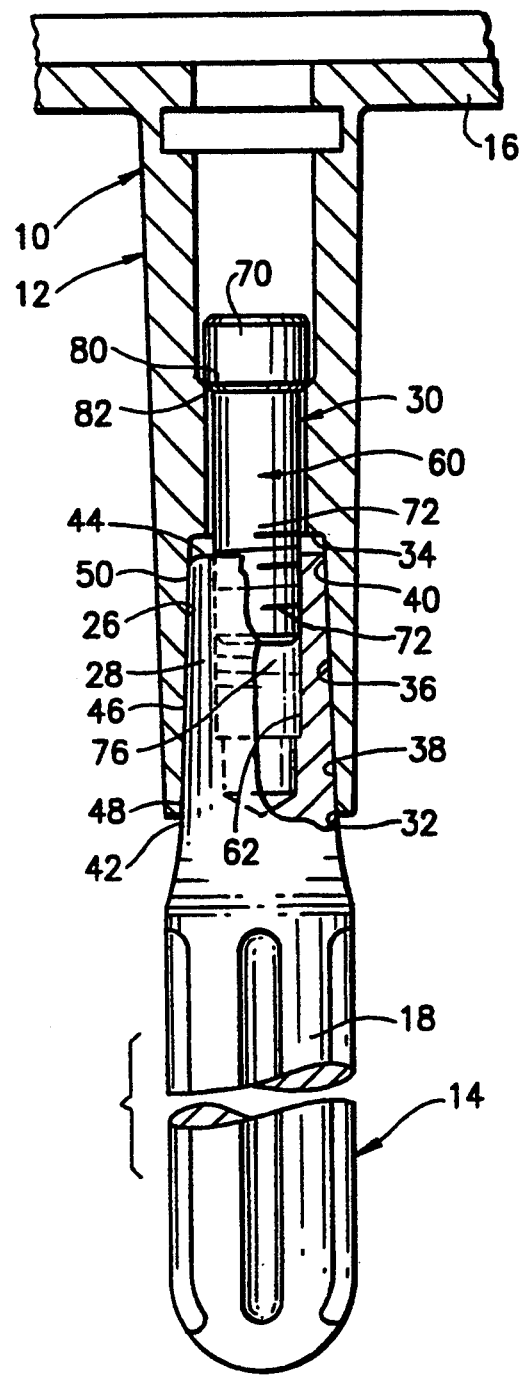
FIG. 4 is an enlarged, fragmentary cross-sectional view showing a portion of the assembled tibial component.

Turning now to FIG. 4, as well as to FIGS. 1 and 2, receptacle 26 extends longitudinally into the tibial tray member 12 between an open end 32 and a remote end 34 spaced longitudinally away from the open end 32. A longitudinally tapered inner surface 36 extends along the receptacle 26 and includes a first, tapered inner surface portion 38 located adjacent the open end 32 and a second, further inner surface portion 40 located adjacent the remote end 34 of the receptacle 26. Post 28 extends longitudinally from the stem 18 of the stem member 14, between a first, or near end 42 at the stem 18 and a second, or far end 44 spaced longitudinally away from the near end 42. A longitudinally tapered outer surface 46 extends along the post 28 and includes a tapered outer surface portion 48 adjacent the near end 42 and a further outer surface portion 50 adjacent the far end 44 of the post 28. Both the tapered inner surface 36 and the tapered outer surface 46 preferably have a frusto-conical configuration. Upon assembly of the tibial tray member 12 with the stem member 14, the post 28 is received and fitted within the receptacle 26 to effect a secure connection between the tibial tray member 12 and the stem member 14.

Figure 7:
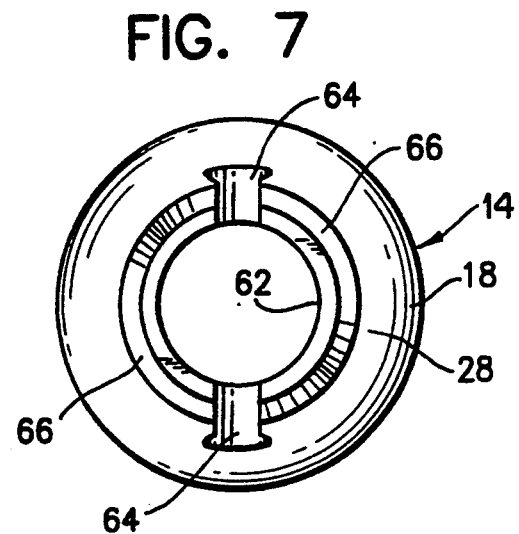
FIG. 7 is a top plan view of one of the parts, taken in the direction of the arrow in FIG. 5.
Figure 5:
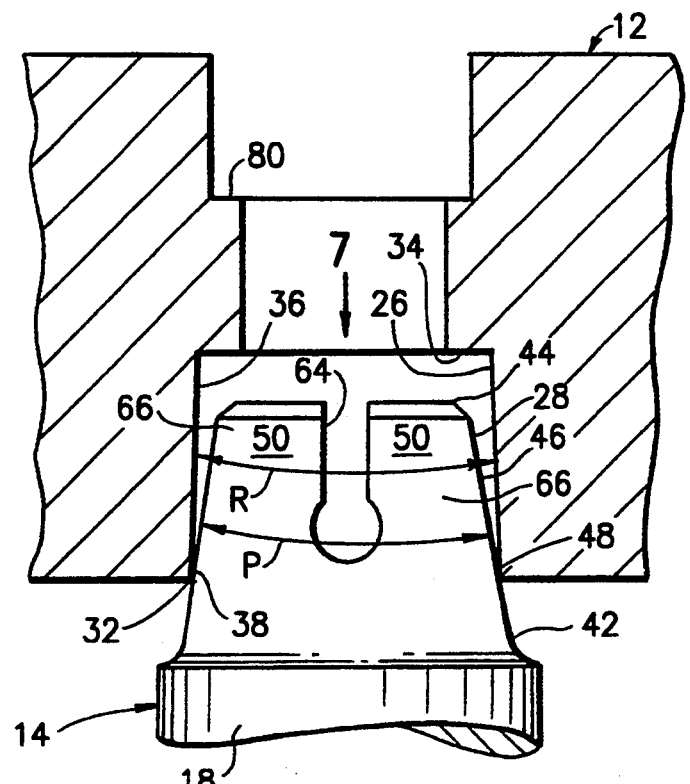
FIGS. 5 and 6 are further enlarged, diagrammatic views of parts of the implant component, exaggerated to show the mechanism by which the parts are assembled.

In order to attain stability in the connection between the tibial tray member 12 and the stem member 14 in the assembled tibial component 10, a stabilizing mechanism 60 is provided in the connection effected between the post 28 and the receptacle 26. As best illustrated diagrammatically in FIGS. 5 and 6, and in FIG. 7, tapered inner surface 36 of the receptacle 26 is provided with a taper angle R, at least along the inner surface portion 38, while tapered outer surface 46 is provided with a taper angle P, at least along the outer surface portion 48. Taper angle R is no greater than, and preferably is slightly less than, taper angle P so that upon insertion of the post 28 into the receptacle 26, at least the inner surface portion 38, adjacent the open end 32 of the receptacle 28, will engage against and will be seated upon the outer surface portion 48, adjacent the near end 42 of the post 28, as seen in FIG. 5. For example, taper angle R may be about 2.8 degrees while taper angle P is between about 2.8 degrees and about 2.9 degrees, and the relative dimensions of the post 28 and the receptacle 26 are such that the post 28 is fitted into the receptacle 26 with inner surface portion 38 seated against outer surface portion 48. In this manner, reception of the greater length of post 28 fully into receptacle 26 is assured.

A generally cylindrical hole 62 extends longitudinally into post 28 from the far end 44 of the post 28 and a lateral slot 64 intersects the hole 62 to establish laterally deflectable portions of the post 28 comprising elements in the form of annular segments 66 spaced circumferentially around the perimeter of the hole 62 at the far end 44. Operator means include the operator member 30 which has a head 70 and an elongate longitudinal operator portion in the form of a shank 72. Deflector means include a helical thread 74 on the shank 72 for engaging a complementary helical thread 76 in the hole 62, along the annular segments 66. A lateral shoulder 80 extends into receptacle 26 adjacent remote end 34 and confronts a seating face 82 on the underside of the head 70 of the operator member 30.

Figure 6:
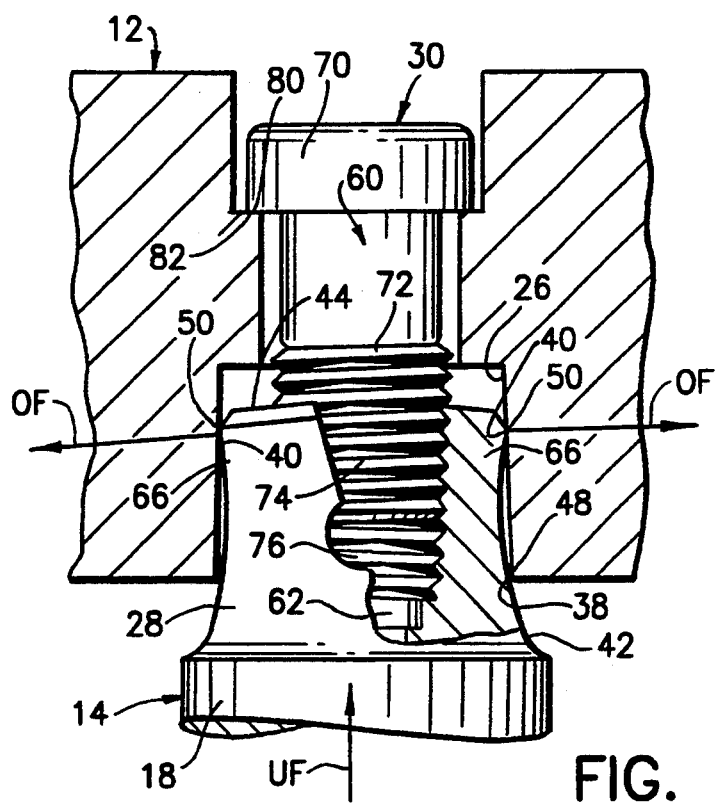

Upon insertion of the post 28 into the receptacle 26 and seating of the inner surface portion 38 on the outer surface portion 48, as seen in FIG. 5, the operator member 30 is advanced longitudinally into the hole 62 by threading the shank 72 into the hole 62, until the seating face 82 on the head 70 of the operator member 30 engages the lateral shoulder 80. As seen in FIG. 6, further operation of the operating member 30 by continued torque on the operating member 30 will establish an upward longitudinal force UF on the post 28, which upward longitudinal force UF, by virtue of the engagement between the helical threads 74 and 76, will result in laterally outward forces OF on the annular segments 66. These laterally outward forces OF will urge the annular segments 66 in laterally outward directions toward engagement with the inner surface 36 at further inner surface portions 40 and, as illustrated in FIG. 6, will deflect the annular segments 66 laterally outwardly into such engagement. At the same time, the inner surface portion 38 is seated firmly against outer surface portion 48. In order to facilitate the laterally outward forces and deflection of the annular segments 66, the longitudinal extent of the annular segments 66, as established by the depth of slot 64, is greater than the longitudinal extent of helical thread 74 into helical thread 76 when the seating face 82 is seated on lateral shoulder 80 and the annular segments 66 are urged into engagement with inner surface 36. In this manner, any lateral movements, such as rocking or toggling movements, of the tibial tray member 12 relative to the stem member 14 are precluded and stability of the connection between the tibial tray member 12 and the stem member 14 in the integrated tibial component 10 is assured.

Figure 8:
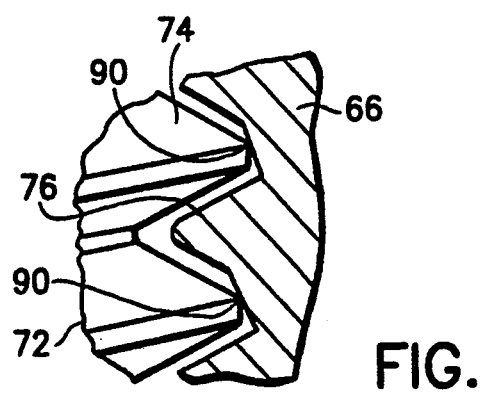
FIG. 8 is a still further enlarged fragmentary view of a portion of FIG. 6, modified to illustrate an alternate embodiment of the invention.

Referring now to FIG. 8, an alternate construction is illustrated for further enhancing the mechanism which attains deflection of the annular segments 66. In the embodiment of FIG. 8, the helical thread 76 which extends along the annular segments 66 is modified to include a supplemental wedge ramp 90, similar to that employed in connection with a thread form available commercially under the trademark SPIRALOCK. The employment of the supplemental wedge ramp 90 not only enhances the laterally outward forces on the annular segments 66, thus enhancing the stability provided by engagement of the laterally outwardly deflected annular segments 66 with the inner surface portion 40, but provides a self-locking mechanism for retaining the operator member 30 in place subsequent to completion of the connection between the tibial tray member 12 and the stem member 14.

It will be apparent that the present invention, as described in detail above, attains the several objects and advantages summarized above, namely: Provides improved integrity in the connection between the members selected for assembly into an integrated component of a prosthetic implant so as to provide enhanced stability in the completed assembly; enables ease of assembly for facilitating the joining together of selected parts into an integrated implant component fitted more closely to the requirements of a particular recipient, without sacrificing the stability provided previously only in unitary, one-piece components; employs a minimum number of individual parts of relatively simple construction for relatively economical manufacture and use; promotes reliability for exemplary performance throughout an extended service life.

It is to be understood that the above detailed description of preferred embodiments of the invention are provided by way of example only. Various details of design and construction may be modified without departing from the true spirit and scope of the invention, as set forth in the appended claims.

The embodiments of the invention in which an exclusive property or privilege is claimed are defined as follows:

1. A modular component for a prosthetic implant, the modular component comprising:
   a first member having a receptacle extending longitudinally into the first member between an open end and a remote end, the receptacle including an inner surface having a longitudinally tapered inner surface portion located between the open end and the remote end of the receptacle;
   a second member having a post extending longitudinally between a near end and a far end spaced longitudinally from the near end, the post including an outer surface having a longitudinally tapered outer surface portion located between the near end and the far end of the post;
   the relative dimensions and relative locations of the tapered inner surface portion and the tapered outer surface portion being such that upon connecting the first member with the second member in appropriate assembled relationship, the inner tapered surface portion is seated upon the outer tapered surface portion adjacent the open end of the receptacle and the near end of the post, with the far end of the post placed adjacent the remote end of the receptacle;
   the post including laterally deflectable portions adjacent the far end of the post; and
   an operator member engageable with the laterally deflectable portions for operation to urge the laterally deflectable portions laterally outwardly relative to the near end of the post toward engagement with the inner surface adjacent the remote end of the receptacle, when the tapered inner surface portion is seated upon the tapered outer surface portion adjacent the open end of the receptacle, to preclude relative lateral movement between the first member and the second member, adjacent the remote end of the receptacle and the far end of the post, and thereby stabilize the connection between the first member and the second member.

2. The invention of claim 1 wherein:
   the tapered inner surface portion extends essentially from adjacent the open end to adjacent the remote end of the receptacle and has a first taper angle;
   the tapered outer surface portion extends essentially from adjacent the near end to adjacent the far end of the post and has a second taper angle; and
   the first taper angle is no greater than the second taper angle so as to assure that the tapered inner surface portion is seated upon the tapered outer surface portion at least adjacent the open end of the receptacle and the near end of the post when the first member and the second member are connected in appropriate assembled relationship.

3. The invention of claim 2 wherein the tapered inner surface portion and the tapered outer surface portion each have a frusto-conical configuration.

4. The invention of claim 3 wherein:
   the post includes a hole extending longitudinally into the post from the far end of the post toward the near end;
   the laterally deflectable portions include generally annular segments on the post, spaced circumferentially around the hole; and
   the operator member includes a longitudinal portion movable longitudinally into the hole, and deflector means on the longitudinal portion for urging the annular segments laterally outwardly in response to longitudinal movement of the longitudinal portion of the operator member into the hole.

5. The invention of claim 4 wherein the hole includes a first helical thread therein along the annular segments, and the deflector means includes a second helical thread for engaging the first helical thread to urge the annular segments laterally outwardly.

6. The invention of claim 5 wherein the first member includes a lateral shoulder adjacent the remote end of the receptacle and the operator member includes a lateral seating face for engaging the shoulder upon threading the second helical thread into the first helical thread such the upon engagement of the seating face with the shoulder, forces exerted by the second helical thread upon the first helical thread will urge the annular segments laterally outwardly.

7. The invention of claim 6 wherein the longitudinal extent of the annular segments is greater than the longitudinal extent of the second helical thread when the seating face is engaged with the shoulder and the annular segments are urged into engagement with the inner surface adjacent the remote end of the receptacle.

8. The invention of claim 6 wherein the configuration of at least one of the first and second helical threads is modified to include means for enhancing the forces exerted by the second helical thread upon the first helical thread to urge the annular segments laterally outwardly, and to provide self-locking engagement between the first and second helical threads.

9. The invention of claim 1 wherein the modular component is a tibial component for a prosthetic knee implant, and:

the first member comprises a tibial tray member having a laterally extending tray;

the second member comprises a stem member having a longitudinally extending stem; and the near end of the post is located at the stem.

10. An improvement in a modular component for a prosthetic implant, in which modular component a first member and a second member are joined to establish an integrated implant component, the improvement comprising:

a post on one of the members, the post extending longitudinally between a first end and a second end spaced away from the first end in a longitudinal direction, the post including an outer surface having a longitudinally tapered surface portion at least adjacent one of the ends of the post and a further surface portion adjacent the other of the ends of the post;

a receptacle in the other one of the members for reception of the post when the members are joined, the receptacle extending between a first end and a second end spaced away from the first end in the longitudinal direction, the receptacle including an inner surface having a first surface portion adjacent one of the ends of the receptacle and generally complementary to the tapered surface portion of the outer surface of the post, and a second surface portion adjacent the other of the ends of the receptacle and for juxtaposition with the further surface portion of the outer surface of the post when the first surface portion of the inner surface of the receptacle is seated against the tapered surface portion of the outer surface of the post;

laterally deflectable elements for placement adjacent the further portion of the outer surface of the post and the second surface portion of the inner surface of the receptacle when the first surface portion of the inner surface is seated against the tapered surface portion of the outer surface of the post; and operator means for urging the laterally deflectable elements laterally relative to the longitudinal direction of the post and the receptacle toward engagement of the further surface portion of the outer surface of the post with the second surface portion of the inner surface of the receptacle, when the first surface portion of the inner surface is seated against the tapered surface portion of the outer surface, to preclude relative movement between the second surface portion and the further surface portion and thereby stabilize the connection between the first member and the second member in the integrated implant component.

11. The invention of claim 10 wherein:

the inner surface of the receptacle is tapered longitudinally essentially from adjacent the first end to adjacent the second end of the receptacle and has a first taper angle;

the outer surface of the post is tapered longitudinally essentially from adjacent the first end to adjacent the second end of the post and has a second taper angle; and the relative dimensions of the post and the receptacle, and the relative magnitude of the first taper angle and the second taper angle are such as to assure that the inner surface is seated against the outer surface at least adjacent one of the ends of the receptacle and the corresponding one of the ends the post when the first member and the second member are connected in appropriate assembled relationship.

12. The invention of claim 11 wherein:

the first end of the receptacle is an open end, and the second end of the receptacle is a remote end spaced away from the open end;

the first end of post is a near end, and the second end of the post is a far end spaced away from the near end;

the first taper angle is no greater than the second taper angle so as to assure that the inner surface is seated against the outer surface at least adjacent the open end of the receptacle and the near end of the post when the first member and the second member are connected in appropriate assembled relationship.

13. The invention of claim 12 wherein the tapered inner surface and the tapered outer surface each have a frusto-conical configuration.

14. The invention of claim 12 wherein the post is located on the first member and the receptacle is located in the second member.

15. The invention of claim 14 wherein:

the post includes a hole extending longitudinally into the post from the far end of the post toward the near end;

the laterally deflectable portions include generally annular segments on the post, spaced circumferentially around the hole; and the operator means includes a longitudinal operator portion movable longitudinally into the hole, and deflector means on the longitudinal operator portion for urging the annular segments in a laterally outwardly direction in response to longitudinal movement of the longitudinal portion of the operator into the hole.

16. The invention of claim 15 wherein the hole includes a first helical thread therein along the annular segments, and the deflector means includes a second helical thread for engaging the first helical thread to urge the annular segments laterally outwardly.

17. The invention of claim 16 wherein the first member includes a lateral shoulder adjacent the remote end of the receptacle and the operator means includes an operator member having a lateral seating face for engaging the shoulder upon threading the second helical thread into the first helical thread such the upon engagement of the seating face with the shoulder, forces exerted by the second helical thread upon the first helical thread will urge the annular segments laterally outwardly.

18. The invention of claim 17 wherein the longitudinal extent of the annular segments is greater than the longitudinal extent of the second helical thread when the seating face is engaged with the shoulder and the annular segments are urged into engagement with the inner surface adjacent the remote end of the receptacle.

19. The invention of claim 17 wherein the configuration of at least one of the first and second helical threads is modified to include means for enhancing the forces exerted by the second helical thread upon the first helical thread to urge the annular segments laterally outwardly, and to provide self-locking engagement between the first and second helical threads.

20. The invention of claim 10 wherein the modular component is a tibial component for a prosthetic knee implant, and:

the first member comprises a tibial tray member having a laterally extending tray;

the second member comprises a stem member having a longitudinally extending stem; and the near end of the post is located at the stem.

* * * * *